(12) United States Patent
Desai et al.

(10) Patent No.: US 7,498,140 B2
(45) Date of Patent: *Mar. 3, 2009

(54) DIRECT DETECTION OF BIOMOLECULES IN A GEL

(75) Inventors: Surbhi Desai, Rockford, IL (US); Craig Smith, Oregon, WI (US); Boguslawa Dworecki, Rockford, IL (US); Steven Moore, Janesville, WI (US)

(73) Assignee: Pierce Biotechnology, Inc., Rockford, IL (US)

( * ) Notice: Subject to any disclaimer, the term of this patent is extended or adjusted under 35 U.S.C. 154(b) by 87 days.

This patent is subject to a terminal disclaimer.

(21) Appl. No.: 11/459,450

(22) Filed: Jul. 24, 2006

(65) Prior Publication Data

US 2006/0252108 A1    Nov. 9, 2006

Related U.S. Application Data

(63) Continuation-in-part of application No. 10/471,273, filed as application No. PCT/US02/06876 on Mar. 7, 2002, now Pat. No. 7,112,411.

(60) Provisional application No. 60/274,264, filed on Mar. 8, 2001.

(51) Int. Cl.
 *G01N 33/53* (2006.01)
 *G01N 27/26* (2006.01)
 *C12Q 1/00* (2006.01)

(52) U.S. Cl. .............................. 435/7.1; 435/4; 204/456

(58) Field of Classification Search ....................... None
See application file for complete search history.

(56) References Cited

U.S. PATENT DOCUMENTS

| 4,582,808 A | 4/1986 | Oosawa et al. |
| 7,112,411 B2 * | 9/2006 | Desai .......................... 435/7.1 |
| 2001/0044108 A1 | 11/2001 | Shih et al. |

OTHER PUBLICATIONS

Desai, et al., "Direct Immunodection of Antigens within the Precast Polyacrylamide Gel," Analytical Biochemistry, 297: 94-98 (2001).
Mohamed, et al., "Polyacrylamide Gel Minaturization Improves Protein Visualization and Autoradiographic Detection," Analytical Biochemistry, 177:287-290 (1989).
Desai, et al., "Immunodetection of Proteins within Polyacrylamide Gels" Bioluminescene & Chemiluminescence Progress and Current Applications Published by World Scientific Publishing Co., 1-4 (Copyright 2002).
Desai, et al., "Alternative to Western Blotting" Recent Res. Devel. Anal. Biochem., 4 (2005) 1-17.

* cited by examiner

*Primary Examiner*—Jon P Weber
*Assistant Examiner*—Paul C. Martin
(74) *Attorney, Agent, or Firm*—Thompson Hine LLP (57) ABSTRACT

A method for detecting a target biomolecule directly in a polyacrylamide gel in which it has been separated from other substances. Prior to binding the target to a probe and while the target biomolecule remains in the gel, the gel is immersed in a water miscible aqueous extracting medium containing a base to shrink the gel by at least about ten percent, and then the gel is washed with water to restore the gel to substantially its original size.

24 Claims, 6 Drawing Sheets
(6 of 6 Drawing Sheet(s) Filed in Color)

DIRECT DETECTION OF BIOMOLECULES IN A GEL

RELATED APPLICATION

This application is a Continuation-In-Part of co-pending U.S. patent application Ser. No. 10/471,273 filed Sep. 8, 2003, which is a National Stage Entry of International PCT Patent file Serial No. PCT/US02/06876 filed Mar. 7, 2002, which is based on U.S. Provisional Patent Application Ser. No. 60/274,264 filed Mar. 8, 2001.

FIELD OF THE INVENTION

A method to directly detect target substances such as proteins in a gel in which they have been separated by electrophoresis.

BACKGROUND

Capture of target substances such as proteins and other biomolecules on solid phases has been used to facilitate their subsequent identification, to study their manner of interacting with other substances, etc. Typical interactions are those between proteins, such as between antigens and antibodies, hormones and receptors, biotinylated molecules and biotin binding proteins, and the like. One method of capture is generally designated as blotting, where the target substance is applied, directly or by transfer from another medium, to a membrane such as nitrocellulose, polyvinyllidene difluoride (PVDF), or nylon.

Blotting is most frequently used in combination with known gel electrophoresis procedures. The target substance, e.g., an antigen, is first separated on a gel from other substances, typically by sodium dodecyl sulfate polyacrylamide gel electrophoresis (SDS-PAGE). The target substance is then transferred electrophoretically to a membrane. Subsequently, the target substance is associated, either directly or indirectly through an intermediate primary ligand, by an affinity interaction to a reporter probe, such as an antibody, having a label attached to it that is capable of providing a detectable signal. Radioactive, calorimetric, fluorescent, or enzymatic labels are commonly employed to provide the detectable signals which, in turn, indicate the presence and/or location of the target substance. Responses from radioactive and fluorescent labels are generally determined directly, while the response (luminescent, fluorescent, or calorimetric) elicited with enzymatic labels is indirect in that the detectable signal results from the action of the enzyme on an appropriate substrate.

Procedures for electrophoretic separation with subsequent blotting onto a membrane are referred to in the literature as Western blotting, Northern blotting or Southern blotting. Western blotting refers to the identification of antigens as target substances, while the latter two procedures refer to identification of target RNA and DNA sequences, respectively. More recently, a variation of Western blotting, referred to as Far Western blotting, has been used to characterize protein-to-protein interactions other than antigen to antibody interactions.

A drawback associated with Western type and other blotting techniques is that they require time consuming and cumbersome steps. These include transferring the target substance from the gel to the membrane on which the substance is immobilized and then blocking the membrane. Some of these steps, particularly the transfer and immobilization operations, may be detrimental to the protein being assayed. For example, a change in antigenic nature of a protein may prevent the corresponding antibody from binding and, therefore, detecting the target molecule. In addition, the pattern obtained on a membrane when a crude lysate is transferred may not be a true representation, since smaller molecular weight proteins transfer more efficiently than larger molecular weight proteins. Additionally, some proteins simply do not transfer well and, therefore, are not represented on the membrane at all.

Thus, in-gel procedures, in which detection is accomplished without removing the target substance from the gel, are desirable. While in-gel techniques for detecting target substances in polyacrylamide gels were reported even before the advent of the above described blotting techniques (Burridge, K. (1976) Proc. Natl. Acad. Sci., USA, 73, 4457-4461; Rosta, J. A.; Kelly, P. T.; and Cotman, C. W. (1977) Anal. Biochem., 80, 336-376; and Olden, K. and Yamada K. M. (1977) Anal. Biochem, 78, 483-490), the procedures were very time consuming, entailing lengthy fixation, incubation and wash steps, which generally took on the order of several days. Furthermore, in-gel techniques have been considered not sufficiently sensitive for the detecting target substances using large reporter probes, e.g., antigen-antibody interactions; the problem was insufficient penetration of the probe or primary ligand into the three-dimensional gel to achieve the required association of the target substance and probe to permit detection at low concentrations of target substance.

It would be desirable to provide an efficient method that is sensitive and useful for in-gel detection of biomolecules.

SUMMARY

In one embodiment, a target substance such as a protein or other biomolecule is separated from other substances by gel electrophoresis and, while the target biomolecule remains in the gel, it is associated either directly or indirectly with a probe having a label that is capable of providing a detectable signal. Any non-associated probe is removed from the gel and the presence of the target biomolecule is detected by observing a signal attributable to the presence of the labeled probe that has remained associated with the target biomolecule. After the target biomolecule has been separated in the gel and prior to initiating the action(s) whereby the target biomolecule becomes associated with the probe, the gel is shrunk by at least about ten percent in one embodiment, and by at least about fifteen percent in another embodiment. One embodiment uses alcohol alone to shrink the gel. Another embodiment uses alcohol and base to shrink the gel. The shrunken gel is then washed with water for a sufficient time to restore the gel to substantially its original size. The assay is then continued with the incubation, wash, and detection steps as conventionally practiced.

Once conventional electrophoresis has been completed, the assay is rapidly completed because there is no need for transfer to a membrane; there is an elapsed time of about 30 minutes from completion of electrophoresis to initial incubation with either primary ligand or directly with probe. This is a shorter time than the typical 2.5-3 hours needed for membrane preparation, transfer, and blocking operations associated with conventional blotting procedures. Because there is no need to transfer or immobilize the separated target biomolecule on a membrane, damage to the target biomolecule is avoided. This method is applicable for direct detection of small quantities of large biomolecules, such as proteins, in the gel.

BRIEF DESCRIPTION OF THE DRAWINGS

This application contains at least one drawing executed in color. A Petition under 37 C.F.R. §1.84 requesting acceptance of the color drawings is filed separately on even date herewith. Copies of this patent or patent application publication with color drawing(s) will be provided by the Office upon request and payment of the necessary fee.

DETAILED DESCRIPTION

The disclosed method is generally applicable to sodium dodecyl sulfate-polyacrylamide gel electrophoresis (SDS-PAGE), where substances are separated by electrophoresis in an aqueous polyacrylamide gel containing sodium dodecyl sulfate. The method is also applicable where substances are separated by electrophoresis in polyacrylamide/agarose, agarose, and glyoxal agarose gels. One embodiment of the method is applicable for the detection of proteins, such as antigens, antibodies, glycoproteins, and other proteins. The method may also be used with biotinylated and other pre-labeled biomolecules separated by gel electrophoresis. Once separated and identified on the gel, the protein bands in the gel can be recovered from the gel for further characterization, identification, etc.

One embodiment of the method detects one or more target biomolecules directly in a polyacrylamide gel. One or more target biomolecules are separated from other substances by electrophoresis in a gel. The gel is shrunk by at least about 10% and then washed with water for a sufficient time to restore the gel to substantially its original size, prior to associating the target biomolecule with the probe and while the target biomolecule remains separated in the gel. The target biomolecule is then associated with a probe having a label that is capable of providing a detectable signal. Any non-associated probe is removed from the gel, and the presence of the target biomolecule is detected by observing a signal attributable to the presence of the labeled probe associated with the target biomolecule.

The method is useful in connection with probes labeled with a variety of entities as previously identified that can directly or indirectly provide a detectable signal. In one embodiment, the signal is colorimetric, radiolabeled, fluorescent, and/or luminescent. The method is also useful in combination with probes containing enzymatic labels that, on contact with a substrate, produce a detectable luminescent and/or fluorescent signal. Horseradish peroxidase (HRP) and alkaline phosphatase (AP) are examples of such enzymes. When HRP is used, the substrate may be luminol.

An example of an enzymatic detection system is described in WO97/39142, published on Oct. 23, 1997, the disclosure of which is hereby incorporated by reference in its entirety, disclosing probes containing HRP as a label. In the presence of a luminol substrate, a source of hydrogen peroxide, and an enhancer, HRP catalyzes an oxidation reaction that yields an intense, long-lasting luminescent signal. The present method, used with this system, enhances the in-gel detection of proteins using large target biomolecules and primary ligands. Systems based on this luminescent technology are marketed by Pierce Biotechnology, Inc. (Rockford Ill.) under the Supersignal® trademark.

Shrinking the gel after electrophoretic separation of the target biomolecule in the gel, but prior to initiating the incubation steps, either directly with the labeled probe or indirectly first with a primary ligand, achieves increased association of the target biomolecule with the probe. In one embodiment, the wet gel is immersed in a water miscible, aqueous extracting medium for a sufficient time to achieve the desired shrinkage. Media comprised of water and a short-chain alcohol, such as methanol, ethanol, and/or isopropanol may be used. Other water miscible components, such as polyethylene glycol, in lieu of or in combination with the alcohol, may also be used. In one embodiment, the target biomolecule is separated by SDS-PAGE and then the gel is pre-treated with a mixture of an alcohol/water and a base such as sodium hydroxide (NaOH). This embodiment resulted in increased detection sensitivity for the target protein. When used in combination with NaOH, the alcohol concentration is about 25% v/v.

In another embodiment, the gel is pre-treated with agarase prior to incubation with the target biomolecule label. The gel can be treated with agarase either prior to gel shrinkage or following gel shrinkage. Agarase can be used either alone or in conjunction with either alcohol or alcohol/base pre-treatment of the gel. In one embodiment, the agarase concentration is from about 0.001 units/μl to about 0.03 units/μl. In another embodiment, the agarase concentration is about 0.0063 units/μl. In one embodiment, the gel is incubated with agarase at about 30° C. to about 50° C. In another embodiment, the gel is incubated with agarase overnight at about 20° C. to about 22° C. In another embodiment, the gel is incubated with agarase for about fifteen minutes at about 45° C.

Alkoxide bases having an alkaline metal where the cation is lithium, sodium, potassium, rubidium and/or cesium, or amine cations where the cation can be Tris base, may be used.

Examples of such bases include LiOH, KOH, and NaOH.

In one embodiment, the alcohol concentration ranges from about 10% v/v to about 75% v/v when used in combination with a base such as NaOH. Using an alcohol (e.g., about 25% v/v alcohol) in combination with a base (e.g., about 1 mM NaOH to about 200 mM NaOH) resulted in enhanced protein detection sensitivity and protein band intensity. For example, 25% v/v alcohol combined with 1 mM NaOH to 200 mM NaOH resulted in five to ten times greater protein detection sensitivity compared with protein detection sensitivity using 25% v/v alcohol without base. It also resulted in two to five times greater protein detection sensitivity, compared with protein detection sensitivity using 50% v/v alcohol without base was used. In one embodiment, the concentration of base ranges from about 25 mM to about 150 mM.

Figure 6:
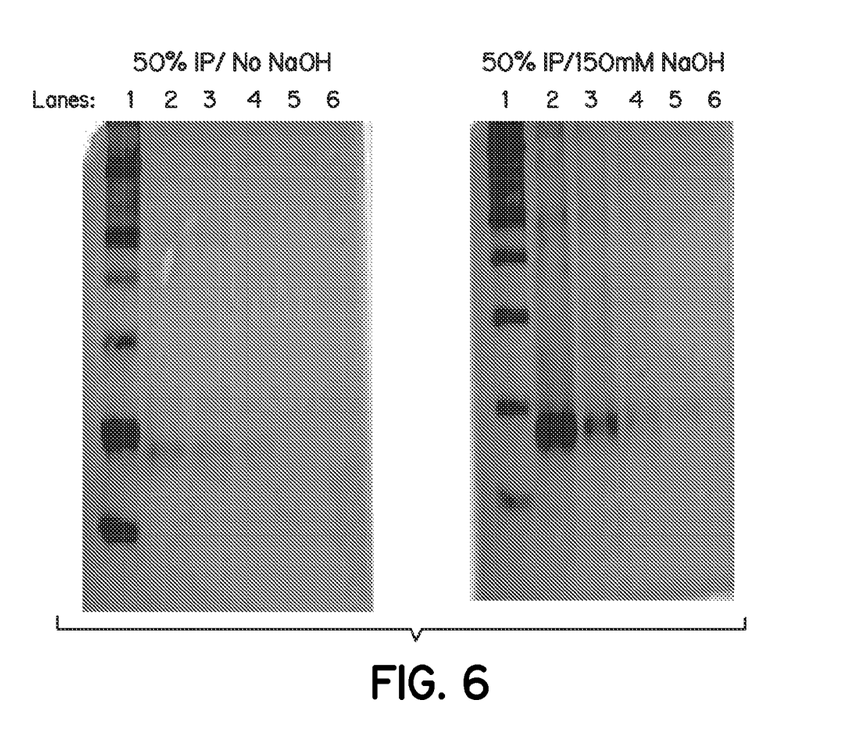
FIG. 6 shows detection of glutathione-S-transferase (GST) using one embodiment of the method.

The effect on detection sensitivity using base in combination with alcohol is shown in FIG. 6. Novex® gels (Invitrogen) were prepared as follows: lane 1, MagicMark™ XP standards (Invitrogen); lanes 2-6: 50 ng, 25 ng, 12.5 ng, 6.25 ng, and 3.125 ng, respectively of GST. Gels containing separated proteins were fixed with a solution of 50% v/v isopropanol with or without 150 mM NaOH, and then incubated with primary rabbit anti-GST antibody followed by goat anti-rabbit IgG Alexa680 conjugated secondary antibody. Stained gels were imaged using a LI-COR Biosciences imager. Fixation with 50% v/v isopropanol alone allowed detection of GST to 12.5 ng. Fixation with 50% v/v isopropanol and 150 mM NaOH increased GST detection to 6.25 ng.

Figure 7:
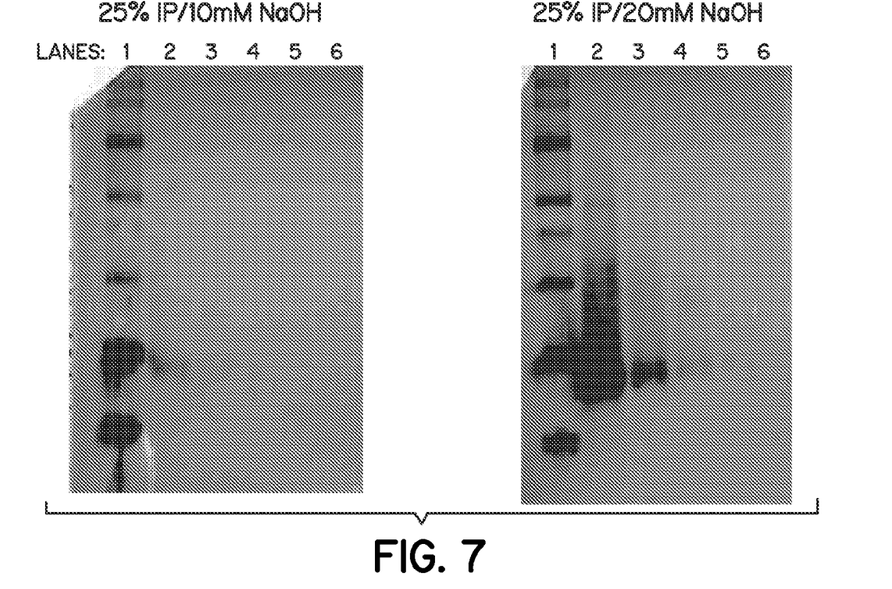
FIG. 7 shows the effect of sodium hydroxide concentrations on GST detection in one embodiment of the method.

The effect of detection sensitivity on GST separated by SDS-PAGE using various concentrations of base in combination with alcohol is shown in FIG. 7. Novex® gels (Invitrogen) were prepared as follows: lane 1—MagicMark™ XP standards (Invitrogen); lanes 2-6: 50 ng, 25 ng, 12.5 ng, 6.25 ng, and 3.125 ng, respectively of GST. Gels containing separated proteins were fixed with a solution of 25% v/v isopropanol with either 10 mM NaOH or 20 mM NaOH, and then incubated with primary rabbit anti-GST antibody followed by goat anti-rabbit IgG Alexa680 conjugated secondary antibody and imaged on a LI-COR Biosciences imager.

In one embodiment, the minimum concentration of NaOH necessary to detect GST using 25% v/v isopropanol was less than about 6 mM NaOH. This effect continued up to about 150 mM NaOH, resulting in detection of 3 ng GST. NaOH concentrations above 150 mM began to decrease detection levels of GST (data not shown). The concentration of base resulting in increased GST detection using 25% v/v alcohol was about 20 mM NaOH. Enhanced detection was obtained using a concentration of base ranging from about 6.25 mM base up to about 200 mM base. However, in another embodiment, enhanced detection was seen with about 1 mM NaOH. A gel treated with 25% v/v isopropanol in combination with 150 mM NaOH resulted in detection of 3.125 ng GST, while a concentration of base exceeding 150 mM decreased detection sensitivity of GST to 6.250 ng (data not shown).

Figure 8:
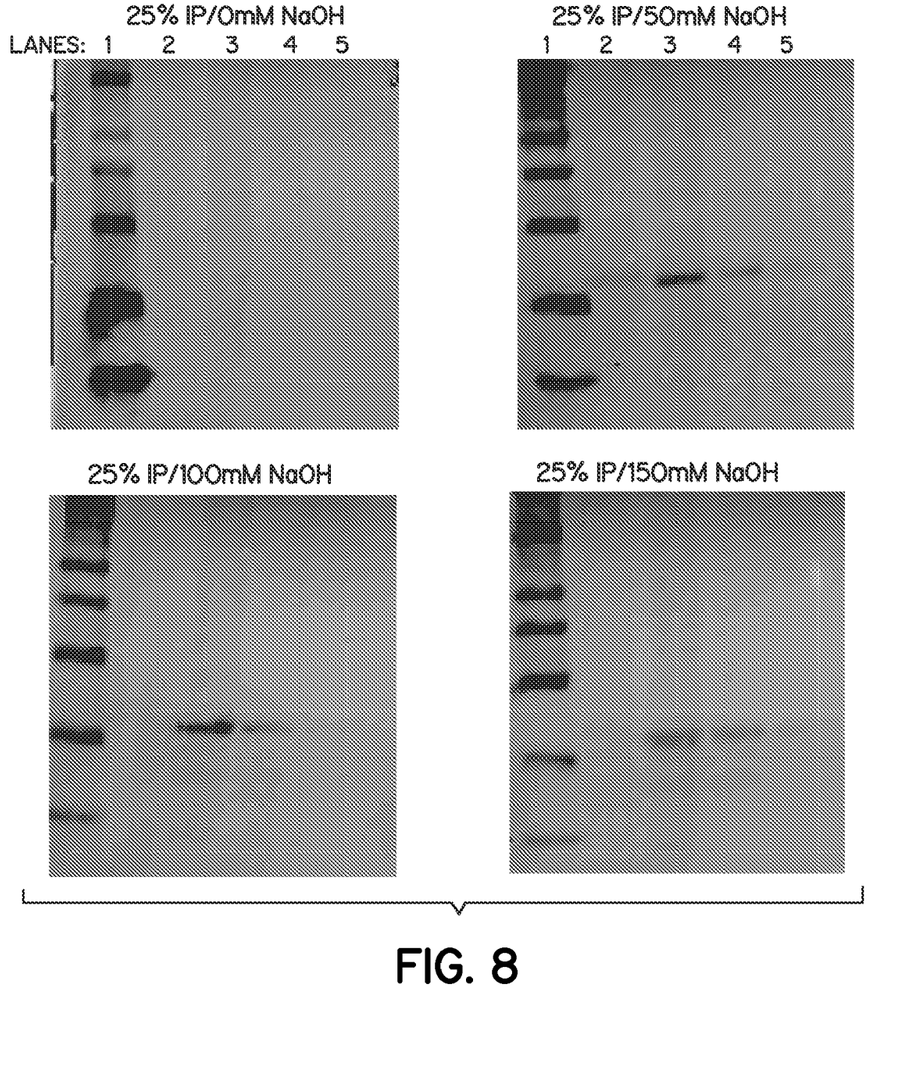
FIG. 8 shows the effect of sodium hydroxide concentrations on IkBα detection in one embodiment of the method.

The effect on Inhibitory Kappa B Alpha (IkBα) detection sensitivity using base in combination with alcohol is shown in FIG. 8. Novex® gels (Invitrogen) were prepared as follows: lane 1, MagicMark™ XP standards (Invitrogen); lane 2, 20 µg A431 cell lysate; lane 3, 20 µg 3T3 cell lysate; lane 4, HeLa cell lysate; lane 5, one-half dilution HeLa cell lysate. Gels containing separated proteins were fixed with a solution of 25% v/v isopropanol and 0 mM, 50 mM, 100 mM, or 150 mM NaOH, respectively, and then incubated with primary rabbit anti-IkBa antibody followed by goat anti-rabbit IgG Alexa680 conjugated secondary antibody and imaged on a LI-COR Biosciences imager.

As shown in FIG. 8, and similar to GST and His tagged proteins, IkBa detection was sensitive to NaOH concentration. IkBa detection sensitivity was enhanced five-fold when the gels were treated with alcohol in combination with increasing concentrations of NaOH.

His tagged protein are proteins containing several (usually six) histidine residues, added to either the N- or C-terminal to facilitate purification of the protein from a lysate using a nickel column. Detection sensitivity of His tagged proteins using base in combination with alcohol is shown in FIG. 9.

Novex® (Invitrogen) or Cambrex Tris Glycine gels were prepared as follows: lane 1, MagicMark™ XP standards (Invitrogen); lanes 2-5, Qiagen His tagged protein ladder dilution series (240 ng, 48 ng, 9.6 ng, 1.92 ng protein, respectively). Gels were fixed with a solution of 25% v/v isopropanol and 0 mM (no base), 50 mM, 100 mM or 150 mM NaOH, as indicated in FIG. 9. Gels were then incubated with primary mouse anti-penta His antibody followed by goat anti-mouse IgG Alexa680 conjugated secondary antibody and imaged on a LI-COR Biosciences imager.

Figure 9:
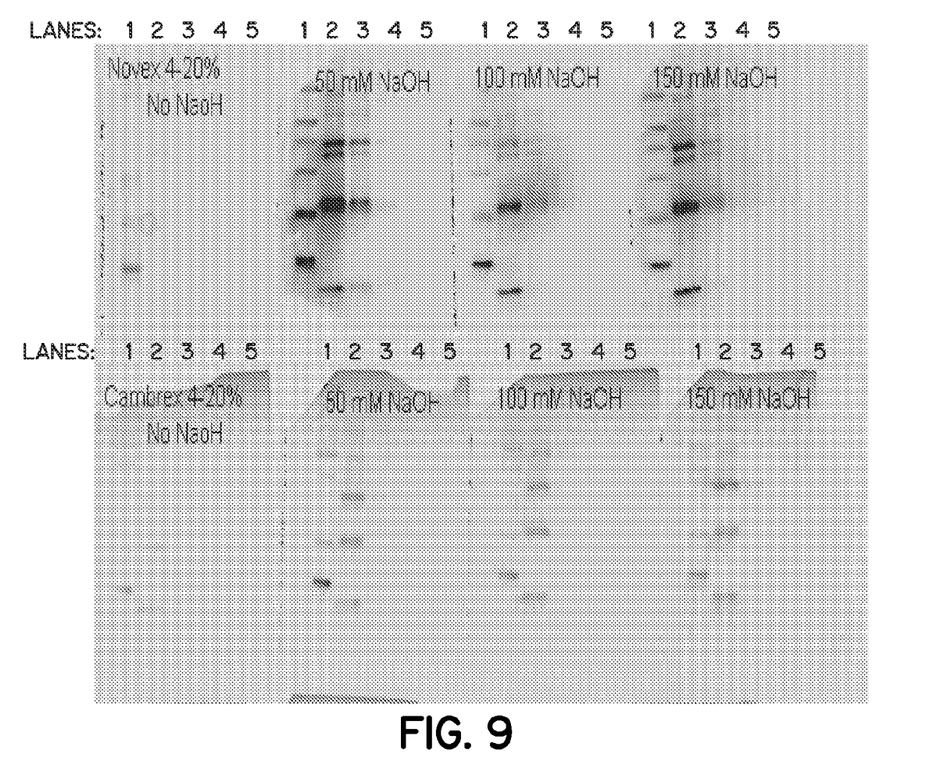
FIG. 9 shows the effect of isopropanol and sodium hydroxide concentrations on detection of His tagged proteins in one embodiment of the method.

As shown in FIG. 9, detection of His tagged proteins was minimal with 25% v/v isopropanol in the absence of base. In gels fixed with 25% v/v isopropanol and 50 mM NaOH, 100 mM NaOH, or 150 mM NaOH, detection was robust, detecting 1.92 ng His epitope in Novex® (Invitrogen) gels. Detection sensitivity was enhanced when the gels were treated with alcohol in combination with NaOH.

The alcohol in the aqueous extracting medium is present in a concentration ranging from about 10% v/v to about 75% v/v. Alcohol concentrations above 75% v/v may shrink the gel excessively, resulting in embrittlement of the gel. Alcohol concentrations lower than 10% v/v may result in inadequate timely shrinkage. In one embodiment, the concentration of alcohol is about 40% v/v to about 60% v/v. In another embodiment, the concentration of alcohol is about 50% v/v.

The alcohol may be methanol, ethanol, isopropanol, propanol, butanol, and/or isobutanol. In one embodiment, the alcohol is isopropanol. In one embodiment, the alcohol is isopropanol at a concentration of about 50% v/v.

The gel is maintained in the alcohol and base for a sufficient time to achieve at least about 10% shrinkage based on the original surface area of the gel. In another embodiment, the gel is maintained in the alcohol and base for a sufficient time to achieve shrinkage of at least about 15%, based on the original surface area of the gel. In another embodiment, the gel is maintained in the alcohol and base for a sufficient time to achieve shrinkage of at least about 20%, based on the original surface area of the gel. Immersion of the gel for about fifteen minutes is ordinarily adequate to achieve the required shrinkage. In one embodiment, to minimize adverse embrittlement, gel shrinkage is less than about 50%. In one embodiment, to minimize adverse embrittlement, gel shrinkage is less than about 35%.

After shrinking, the shrunken gel is washed with water, alone or as an aqueous buffer. This wash removes the extracting medium from the gel and rehydrates the gel to restore it to substantially its original size, i.e., either the same or slightly (about 5%) smaller or larger than its original size, generally slightly larger. While any manner of washing can be employed, in one embodiment, washing is accomplished using a colander designed for gel detection procedures.

Once size restoration is accomplished by re-hydration through washing, the gel can then be directly incubated in a solution containing the labeled target probe. Alternatively, if an indirect, sandwich approach is utilized, incubation can first occur in a solution containing a primary ligand having specific affinity for the target biomolecule, followed by a second incubation in a solution containing a reporter probe having affinity for the primary ligand. In either instance, the probe becomes selectively associated with the target biomolecule. At various stages, including the pre-treatment and probe-incubation steps, sensitivity/intensity of the assay can be enhanced by sonicating the gel. Subsequent to incubation(s), the assay can be completed following conventional practices of washing and eliciting a response.

Any gel useful in electrophoresis applications, such as SDS-polyacrylamide, which are either commercially available (e.g., Novex®, Invitrogen) or individually prepared, may be used. The gels can be either homogeneous or gradient and include pre-cast, Tris-Glycine, Bis-Tris, Tris-Acetate and Tricine gels. In one embodiment, individually prepared or home-made gels are used and the siliconization procedure used to treat the plates in which the gel is cast affects the alcohol used in for gel pretreatment. In one embodiment, the plates are siliconized with aminotriethoxysilane and the alcohol used for gel pretreatment is methanol. In another embodiment, the plates are siliconized with RainX® and the alcohol used is isopropanol.

While the method has been described with reference to one-dimensional electrophoresis, it is equally applicable with respect to electrophoresis accompanying two-dimensional (2D) separations. In 2D separations, the step of gel electrophoresis is preceded by a separation of substances by isoelectric focusing. The 2D procedure is most useful when gel electrophoresis in the first dimension alone is not sufficient to separate target biomolecules. The method is suitable for multiplexing, where multiple detection moieties are employed in a single gel, as further described in example IX below.

In one embodiment, the method provided enhanced sensitivity to other protein detection methods. For example, the method enhanced general protein stains as well as group-specific protein stains (e.g., phosphoproteins, glycoproteins, etc.) in protein-protein interaction (Far Western blot) and lectin-glycoprotein interactions.

The following examples further illustrate the method. The reagents and materials used in the examples are as follows:

Pure glutathione-S-transferase (GST) and anti-GST, rabbit polyclonal IgG were obtained from Santa Cruz BioTechnology (Santa Cruz, Calif.). E. coli bacterial cell lysate expressing recombinant mouse Id-1: GST mouse Id-2:GST and mouse Id-3:GST lysates were from PharMingen (San Diego Calif.). Id proteins are generally described in Kadesch, T. (1993) Cell Growth Differ., 4, 49-55. Mouse anti-penta-His antibody and the His tag ladder were from Qiagen (Chatsworth Calif.). Living Color A.v. peptide antibody specific for green fluorescent protein (GFP), rabbit anti-6xHis antibody, and GFP monoclonal antibody were from ClonTech (Palo Alto Calif.). Tris-Glycine SDS sample buffer (2×) was from Novex (San Diego Calif.). 9H-(1,3 dichlor9,9-dimethylacridin-2-one-7-yl)-phosphate (DDAO-phosphate) and goat anti-rabbit alkaline phosphates were from Molecular Probes (Carlsbad Calif.). Enhanced chemiluminescence (ECL) was obtained from Amersham Pharmacia Biotech. (Piscataway N.J.) The Developer/Replenisher and the Fixer/Replenisher were obtained from Sigma Chemical Corporation (St. Louis Mo.). Gradient and homogeneous Tris-Glycine polyacrylamide gels were obtained from Novex.

The following materials were obtained from Pierce Biotechnologies Inc. (Rockford Ill.): streptavidin, HRP-labeled; Y-Per® yeast protein extraction reagent; phosphate-buffered saline (PBS); Tris-buffered saline (TBS); Tween®-20; goat anti-rabbit, HRP labeled; goat anti-mouse, HRP labeled; electrophoresis buffer; bovine serum albumin (BSA); Supersignal® West Dura Extended Duration Substrate (stable peroxide buffer and luminol enhancer); isopropanol; exposure film and magnesium chloride. The yeast cells and lysates (GFP & GST) and the bacterial lysate (GFP/6xHis tagged) were prepared by conventional techniques known to one skilled in the art. Mycobacterium Complex (bacterial complex that binds proteins in human respiratory epithelial cells in Tuberculosis) strain 101 (MAC 101) lysate and biotinylated human respiratory epithelial cell extract (B-Hep-2) were from Dr. Venkata Reddy, School of Medicine at University of Illinois at Chicago, Rockford, Ill.

Gel sample preparation and SDS-PAGE electrophoresis were accomplished as follows. Pure protein samples were prepared by dilution in the sample buffer such that the final protein concentration was 0.1 ng/µl to 1 ng/µl. For Example V, MAC 101 lysate was diluted so that the final concentration was from 0.5 ng/µl to 1.5 µg/ml. Other lysate samples were diluted 1:10-1:1,000 in 2× sample buffer (containing Tris glycine, SDS and glycerol). All of the samples were heated at 95° C. for 5 minutes and cooled before loading onto the gels, either 4-20% or 10-20% Tris-Glycine. The samples were separated by analytical mini-gel SDS-PAGE using the Novex® system at 120 V until the dye front reached halfway down, then at 180 V until the dye front reached the bottom of the gel.

The following examples illustrate both an indirect assay protocol using a primary antibody (the primary ligand) for initial association with the target protein followed by incubation with a labeled secondary antibody (the reporter probe), which binds to the primary antibody and in a direct assay protocol in which the reporter probe is directly associated with the target. Example VIII illustrates the use of the inventive method in conjunction with 2D gel electrophoresis and example IX shows the use of the inventive method for detection of glycoproteins.

EXAMPLE I

Proteins were separated on a 4-20% Tris-Glycine gel. The proteins were pure GST mouse Id1:GST lysate, and yeast GST lysate. The gel containing separated proteins was incubated for 15 minutes in 50 ml of 50% v/v isopropanol/$H_2O$ to achieve about 20% shrinkage and then washed with 100 ml $H_2O$ (Milli-Q®) for fifteen minutes to restore the gel to substantially its original size. The gel was then incubated with 20 ml rabbit anti-GST (starting concentration of 0.2 mg/ml) diluted (1:1,000) in 1% BSA/PBS/0.05% Tween®-20, for one hour at room temperature, about 20° C. to about 22° C. The gel was washed 3×10 minutes with 100 ml PBS/0.05% Tween®-20. An HRP-labeled secondary antibody [goat anti-rabbit antibody/HRP (GAR/HRP)] stock solution at 10 µg/ml was diluted 1:500 in 1% BSA/PBS/0.05% Tween®-20. The diluted antibody solution (20 ml) was added to the gel. The gel was incubated for one hour at RT and then washed 3×10 minutes with 100 ml PBS/0.05% Tween®-20. The gel was incubated for five minutes at RT in 10 ml of the Supersignal® substrate working reagent. The gel was washed for fifteen seconds with Milli-Q® Water. The gel was placed between cellophane sheets and exposed to film for different lengths of time. The film was developed using the Developer/Replenisher and Fixer/Replenisher, as previously described.

Figure 1:
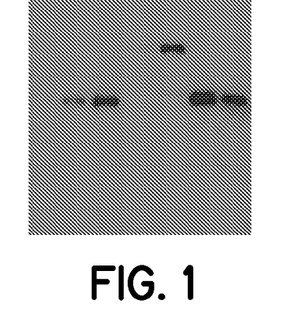
FIG. 1 shows the developed film that was exposed to the gel after completion of the assay in Example I.

FIG. 1 shows the developed film from the assay conducted according to Example I. Lanes 1, 2 and 3 correspond to 1 ng, 5 ng, and 10 ng pure GST, respectively. Lanes 4 and 5 correspond to GST lysate:Id-1 (Santa Cruz Biotech) diluted 1:100 and 1:10, respectively. Lanes 6 and 7 correspond to yeast GST lysate (Pierce) diluted 1:10 and 1:100, respectively. Sensitivity down to 1 ng, with low background, is obtained in this assay using GST and anti-GST.

EXAMPLE II

Example I was repeated except that pure GFP/6xHis tagged proteins, GFP/6xHis expressed in bacterial cell lysate, and GFP expressed in yeast lysate were used as targets and the primary antibody used was the rabbit anti-living color antibody. The assay took about 3.5 hrs to complete after electrophoresis. A conventional western blot assay was performed taking about 6.5 hrs after electrophoresis, on the same target molecules, with detection being accomplished with an ECL chemiluminescent substrate (Amersham Pharmacia Biochem).

Figure 2A:
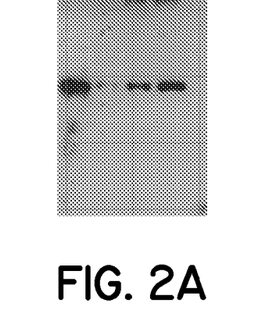
FIG. 2A shows the developed film that was exposed to the gel after completion of the assay in Example II.
Figure 2B:
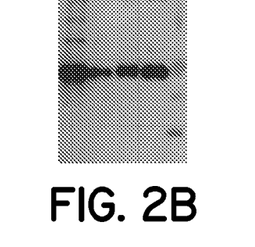
FIG. 2B shows the developed film that resulted from a conventional Western blot.

FIG. 2 compares the in-gel detection protocol (FIG. 2A) with the conventional Western blot protocol using ECL as a detection substrate (FIG. 2B). Lane 1 corresponds to GFP/6xHis-tagged lysate diluted 1:100 and lanes 2, 3, and 4 correspond to 1 ng, 5 ng, and 10 ng pure GFP/6xHis-tagged, respectively. Lane 5 corresponds to Blue Ranger Molecular Weight Marker (Pierce Biotechnologies, Inc.). For in-gel detection, the gel was pretreated with 50% v/v isopropanol for fifteen minutes and then washed with water for fifteen minutes. For the Western blot, the samples were transferred from the gel to the membrane using a Bio-Rad Transfer unit at 200 mA for two hours. The Western blot was blocked overnight with 1% BSA (w/v in PBS/Tween® containing 0.05% Tween®-20 (PBST)). The gel and the Western blot were then incubated for one hour with anti-penta His antibody (Qiagen). The antibody concentration used for the gel and the Western blot was 0.2 µg/ml and 0.1 µg/ml, respectively. The gel and the membrane were washed 3×10 minutes with PBST. The gel and the membrane were then incubated with goat antimouse HRP at 0.02 µg/ml and 0.01 µg/ml, respectively. Both the gel and membrane were washed 6×5 minutes with PBST and then they were incubated for five minutes with the working reagent for SuperSignal Dura (Pierce Biotechnologies, Inc.) and ECL (GE), respectively. The gel was rinsed with water for fifteen seconds. Both the gel and the membrane were then placed in between cellophane and exposed to film. Finally, the films were then developed with Fixer and Developer (Sigma).

The results of the two detection protocols were comparable but, as noted above, the time needed to complete the in-gel detection assay was substantially shorter and involved fewer manipulative steps. The results also show that the Western blot shows considerable non-specific binding in Lane 1 (only the intense band is the specific one) and with the pre-stained MW Markers in Lane 5.

EXAMPLE III

Figure 3A:
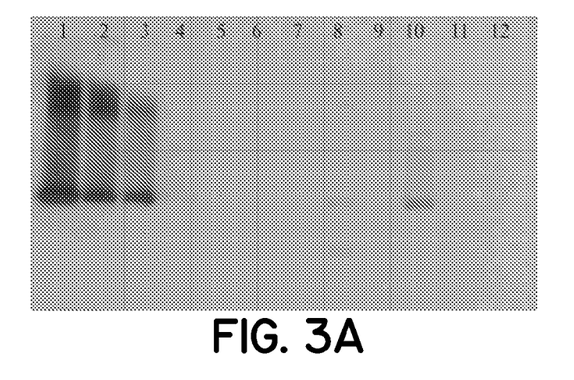
FIG. 3A shows the developed film that was exposed to the gel after completion of the assay in Example III and probed with anti-living color primary antibody and detected with goat anti-rabbit antibody:horseradish peroxidase (HRP)
Figure 3B:
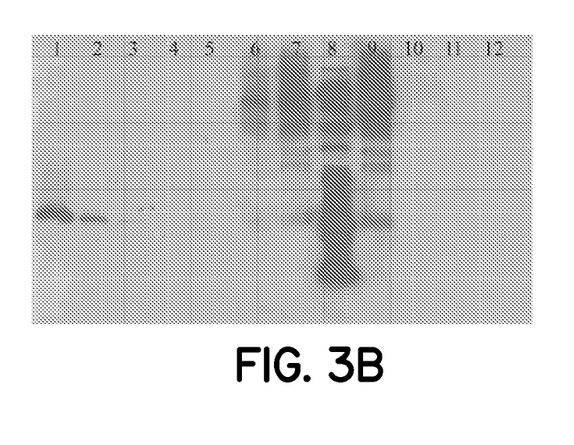
FIG. 3B shows the developed film that was exposed to the gel after completion of the assay in Example III and probed with anti-penta-His primary antibody and detected with goat anti-mouse antibody:HRP.

Pure GFP/6XHis tagged protein, 6X His-tagged ladder (Qiagen) and pure GFP were separated as described in Example II except that one gel (4-20%) was probed with anti-GFP primary antibody, at 2 µg/ml, and detected with goat-anti rabbit antibody:HRP (FIG. 3A) and another gel probed with anti-penta-His primary antibody. at 0.2 µg/ml, followed by goal-anti mouse antibody:HRP at 0.4 µg/ml (FIG. 3B). Lanes 1-5 correspond to 20 ng, 10 ng, 5 ng, 1 ng and 0.5 ng pure GFP/6xHis-tagged, respectively. Lanes 6, 7, and 9 correspond to 6 X His-tagged ladder at 1:16, 1:8 and 1:4 respectively. Lane 8 corresponds to MagicMark "XP" Standards (Invitrogen). Lanes 10, 11, and 12 correspond to 2.5 ng, 1 ng, and 0.5 ng pure GFP, respectively.

As shown in FIGS. 3A and 3B, protein detection using the in-gel method was specific for the antigen being probed; a specific signal was obtained in response to the primary antibody used in the assay. The Example shows that pure GFP, which does not express a 6xHis tag, was not detected by the anti-Penta His antibody.

EXAMPLE IV

The Tris-Glycine gel (10-20%), prepared as in Example II, with separated GFP/6xHis pure protein, bacterial cell lysate expressing GFP/6xHis, and yeast lysate expressing GFP, was incubated for fifteen minutes with 50 ml of 50% v/v isopropanol/H$_2$O and then washed with 100 ml H$_2$O (Milli-Q®) for fifteen minutes. The gel was then incubated in 20 ml HRP conjugated Anti-6 XHis Antibody at 0.2 µg/ml diluted in 1% BSA/PBS/0.05% Tween®-20, for one hr at RT. The gel was washed 3×10 minutes with 100 ml PBS/0.05% Tween®-20. The gel was then incubated for five minutes at RT in 10 ml Supersignal® Substrate working reagent. The gel was washed for fifteen seconds with Milli-Q® Water. The gel was placed between cellophane sheets and exposed to an Alpha Innotech CCD camera.

Figure 4:
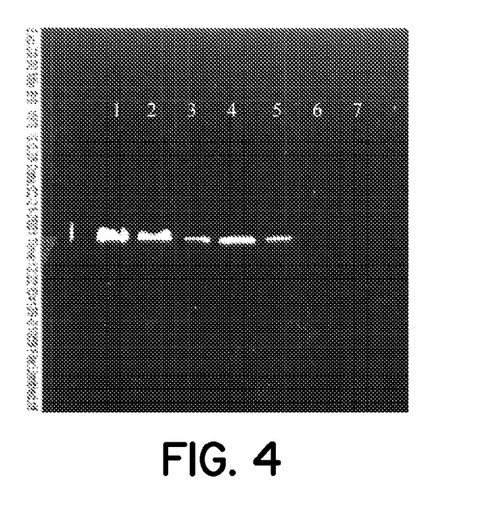
FIG. 4 shows the image capture from a CCD camera of the gel after completion of the assay in Example IV.

As shown in FIG. 4, a directly labeled primary antibody was used to detect antigens directly in the gel. Lanes 1, 2 and 3 correspond to 10 ng, 5 ng, and 1 ng pure GFP/6xHis-tagged, respectively. Lanes 4 and 5 correspond to *E. coli* GFP/6xHis-tagged lysate diluted 1:100 and 1:1,000, respectively. Lanes 6 and 7 correspond to yeast GFP lysate 1:10 and 1:100, respectively. As in Example III, the antibody did not recognize the yeast GFP that does not express the His tag.

Examples V and VI illustrate the method where the target is a protein in a cell lysate using either an indirect (Example V) or direct (Example VI) assay.

EXAMPLE V

Proteins in *Mycobacterium avium* complex lysate (MAC 101) diluted in sample buffer, at 15 µg/lane, and 7.5 ug/lane, were separated on an 8-16% gel, as described previously. Duplicate samples of each lysate were separated on two different sides of the gel. The gel was incubated for fifteen minutes with 50 ml of 50% v/v isopropanol/water and then washed with 100 ml (Milli-Q®) water for fifteen minutes. The gel was then cut in half through the middle so that each half of the gel contained the lysate samples. One of the gel halves was incubated in 20 ml biotinylated human respiratory epithelial (B-Hep-2) cell extract at a starting concentration of about 0.5 mg/ml and then diluted 1:200 in 1×1% BSA/PBS/05% Tween®-20 for one hr at RT. The other of the gel halves was incubated in 1% BSA/PBS/05% Tween®-20 for one hr at RT. The gel halves were washed 3×10 minutes with 100 ml PBS/05% Tween®-20. Both gel halves were then incubated in 20 ml HRP-labeled Streptavidin solution, at 1 mg/ml, diluted 1:25,000 in 1% BSA/PBS/05% Tween®-20, for one hr at RT. The gel halves were washed 3×10 minutes with 100 ml PBS/05% Tween®-20. The gel halves were incubated for five minutes in 10 ml Supersignal® substrate working reagent and then washed with Milli-Q® water for fifteen seconds. The gel halves were placed in between cellophane and exposed to X-ray film for different lengths of time. The film was developed using the Developer/Replenisher and Fixer/Replenisher solutions.

Figure 5A:
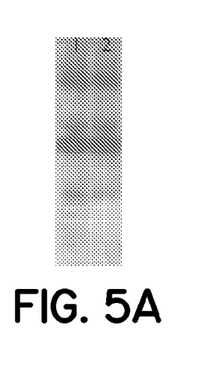
FIGS. 5A, 5B show indirect detection of a target protein from a cell lysate using one embodiment of the method.
Figure 5B:
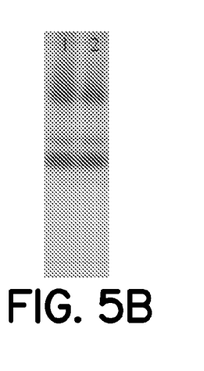

As shown in FIG. 5, a band corresponding to a 31 kD protein was observed in the gel incubated with B-Hep-2 extract. This was due to a reaction between a protein in the B-Hep-2 extract and a protein in the MAC 101 lysate. Additional endogenous biotin bands were observed both in the control gel (FIG. 5B), which was not incubated with the B-Hep-2 extract, and the gel incubated with the B-Hep-2 extract (FIG. 5A).

EXAMPLE VI

Yeast cells ($1\times10^6$) were washed 3×1 ml with PBS. The cells were divided into 3 microcentrifuge tubes before the last wash. PBS (100 µl) was added to each tube after the last wash. The cells in two of the tubes were biotinylated with 5 ul of NHS-LC-Biotin (at 10 mg/ml in DMF) and Sulfo-NHS-LC-Biotin (at 10 mg/ml in Milli-Q® water) respectively, for one hr at 37° C. No biotinylation reagent was added to the third tube. The cells were washed 2×1 ml with PBS, using a microcentrifuge at 10,000 rpm for five minutes to separate the cells from the wash buffer. The cells were then lysed with 100 µl of Y-PER® (Yeast Protein Extraction Reagent)(Pierce Biotechnologies Inc.) for twenty minutes at RT. The lysed cells were centrifuged for five minutes in a microcentrifuge at 10,000 rpm to remove any debris and then mixed 1:3 with 2× Novex Tris-Glycine SDS sample buffer and heated for five minutes at 95° C. Each sample (10 µl) was applied to a 4-20% gel and proteins were separated by electrophoresis, as described previously.

The gel containing the separated proteins was incubated for fifteen minutes with 50 ml of 50% v/v isopropanol and then washed with 100 ml (Milli-Q®) water for fifteen minutes. The gel was then incubated in 20 ml HRP-labeled Streptavidin solution, at 1 mg/ml, diluted 1:250,000 in 1% BSA/PBS/05% Tween®-20. The gel was washed 3×10 minutes with 100 ml PBS/05% Tween®-20. The gel was incubated for five minutes in 10 ml SuperSignal® substrate working reagent and then washed with Milli-Q® water for fifteen seconds. The gel was placed in between cellophane and exposed to X-ray film for different lengths of time. The film was developed using the Developer/Replenisher and Fixer/Replenisher solutions.

The results showed that different protein bands were observed for the cells biotinylated with the NHS-LC-Biotin compared to those biotinylated with the water-soluble Sulfo-NHS-LC-Biotin. The biotinylation of the different proteins with these reagents distinguished between integral membrane proteins, biotinylated with the membrane soluble NHS-LC-Biotin, and the cell surface proteins, biotinylated with the water soluble, but membrane insoluble, Sulfo-NHS-LC-Biotin. These results showed that it was possible to distinguish between cell surface proteins and integral membrane proteins using the method. The control experiment did not show any protein bands in response to the Streptavidin-HRP detection.

While the foregoing examples have employed the chemiluminescent substrate, luminol, and HRP, the following example, Example VII, illustrates the use of the method with the acridine based fluorogenic substrate, DDAO-phosphate, together with alkaline phosphatase.

EXAMPLE VII

Pure GST and mouse Id1:GST, Id2:GST and Id3:GST lysates were separated by electrophoresis in a 10-20% Tris-Glycine gel, as described in Example I. The gel containing the separated proteins was incubated for fifteen minutes in 50 ml of 50% v/v isopropanoL/$H_2O$ and then washed with 100 ml $H_2O$ (Milli-Q®) for fifteen minutes. The gel was then incubated in 20 ml rabbit anti-GST, diluted (1:1000) in 1% BSA/TBS/0.05% Tween®-20, for one hr at RT. The gel was washed 3×10 minutes with 100 ml TBS/0.05% Tween®-20. An alkaline phosphatase labeled secondary antibody (goat anti-rabbit antibody/alkaline phosphatase stock solution at 2 mg/ml) was diluted 1:1,000 in 1% BSA/TBS/0.05% Tween®-20. The diluted antibody solution (20 ml) was added to the gel. The gel was incubated for one hr at RT and then washed 2×10 minutes with 100 ml TBS/0.05% Tween®-20 and 1×10 minutes with 10 ml TBS (pH 9.5) containing 1 mM $MgCl_2$. The gel was incubated for fifteen minutes at RT in 10 ml DDAO-phosphate substrate working solution [DDAO-phosphate was reconstituted at 1.25 mg/ml and then diluted 1:1,000 in TBS (pH 9.5) containing 1 mM $MgCl_2$]. The substrate was removed and the gel was scanned using a Typhoon instrument (GE Healthcare). The instrument was set at 646 nm absorbance maxima and 659 emission maxima.

All the samples, pure GST and GST lysates, were detected with this method. Thus, the example illustrates the feasibility of the method with fluorescent substrates.

EXAMPLE VIII

Example VIII shows the use of the inventive method in 2D gel electrophoresis (2DGE) applications. This method is often used for the separation and identification of proteins in a complex mixture using two separate dimensions that are performed perpendicularly and separately to one another. This allows a complex biological sample to be separated over a larger area, increasing the resolution of each component when compared to a 1D SDS-PAGE gel. The technique is well suited to the large-scale identification of a significant number of proteins in a sample, such as an investigation of global protein expression of an organism or a specific tissue. 2D gels also allow for rapid protein identification using mass spectrometry to generate peptide fingerprint data. Another use of 2D gels is differential expression. This technique compares two or more samples to study differences in their protein expression due to the changing parameter(s), an example being diseased and healthy tissues differentially examined to elucidate proteins responsible for the pathology of disease, or the effects of a drug on treated versus untreated tissue samples.

The first dimension of a 2D gel uses isoelectric focusing (IEF) which separates proteins based on their charge (pI) which is a property of a protein due mainly to the amino-acid composition (number of acidic and basic residues). IEF uses pH gradients that can be established by adding ampholytes or immobilines to an acrylamide gel. The second dimension of a 2D gel separates proteins based on their size (molecular weight). A number of gel gradient (polyacrylamide SDS-PAGE) concentrations and different buffering systems can be used in the second dimension. This method is essentially the same as a 1D SDS-PAGE gel where proteins are separated by mass.

Sample preparation for 2D gel electrophoresis generally requires the use of a buffer that solubilizes and denatures proteins, which is used to separate proteins into individual species and improves the separation by IEF. Urea is a commonly used chaotrope in 2DGE and is found in most solubilization buffers. Urea disrupts hydrogen and hydrophobic bonds, and has no effect on the native charge of a protein. To fully denature proteins, the disulfide bonds within the polypeptide chain, or between sub-units of a complex must be disrupted. This is accomplished using a reductant, such as dithiothreitol or dithioerythritol, which facilitates conversion of disulfide bonds to free sulfhydryl groups. The sulfhydryls are then alkylated with iodoacetamide to prevent reversal and re-formation of the sulfhydryl bridges. The solubilization buffer also includes detergents that serve a number of purposes including, disruption of membranes, solubilization of lipids and delipidation of proteins bound to membranes or vesicles. After solubilization, a low pH organic solvent extraction (precipitation) may be required to remove problematic components such as salts and excess detergent. Following solubilization, the samples may be centrifuged before IEF to sediment particulates that can cause smearing and blockage of the polyacrylamide gel matrix.

After the samples have been subjected to IEF (first dimension) and mass separation (second dimension), the gel is subjected to the method, using both direct and indirect detection methods.

EXAMPLE IX

Post-translation modifications play an important role in many cell functions; glycosylation is the most common and complex modification. It affects many cell functions including protein folding, activity, regulation, stability and solubility. Changes in protein glycosylation trigger diseases such as cancer, cystic fibrosis, congenital disorders and autoimmune disorders. Glycoproteins can be detected within the gel using lectins. Lectins used for probing the gel can either be labeled directly or indirectly (with biotinylated lectins and labeled streptavidin) with a reporter.

A glycoprotein molecular weight standard set, CandyCane™ (Invitrogen), was separated on 4-20% Tris-Glycine gels. Following a five-minute water rinse, the gel was incubated in a 25% v/v isopropanol and 25 mM NaOH fixing solution for fifteen minutes. The gel was then washed twice with water for five minutes each followed by incubation with biotinylated lectin in a 0.25% w/v polyethylene glycol (PEG) solution for one hour. The gel was then washed three times with PBS-0.05% v/v Tween®-20 for ten minutes each. Following incubation of the gel with DyLight™-649 labeled Streptavidin in 0.25% w/v PEG for one hour, the gel was washed with PBS-0.05% v/v Tween®-20 five times for five minutes each and one wash for five minutes with PBS alone, and visualized on Typhoon (GE Healthcare).

Figure 10:
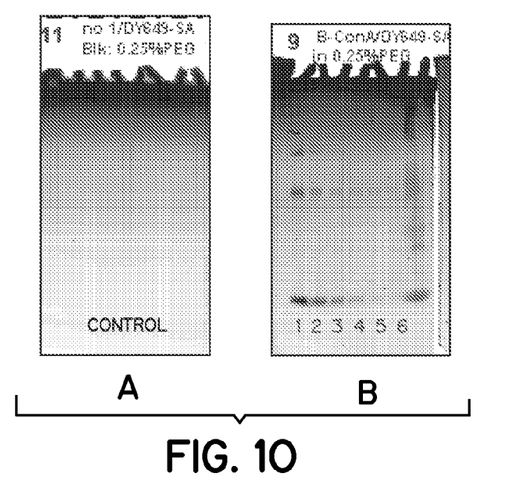
FIG. 10 shows detection of glycoproteins with one detection system in one embodiment of the method.

In FIG. 10, the CandyCane™ marker set was loaded on the gel as follows: lanes 1 to 6 correspond to 31.3 ng, 15.6 ng, 7.8 ng 3.9 ng, 2.0 ng, and 1.0 ng, respectively. Lane 7 contains ProteoProfile Marker (Sigma-Aldrich).

The probes were diluted in 0.25% w/v 15-20K PEG (FIGS. 10A and 10B). Gel in panel A was incubated in 0.25% w/v 15-20K PEG (Control) and the gel in panel B was incubated in biotinylated Concanavalin A (ConA)(1:500 of 1 mg/ml). Further, both gels were incubated with DyLight™ 649-Streptavidin (SA)(1:2500 of 1 mg/ml). The results show detection of all of the glycosylated proteins containing glucose and mannose sugar residues using this detection system.

Figure 11:
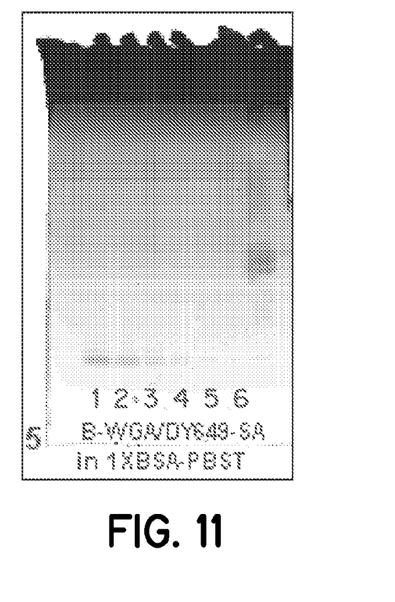
FIG. 11 shows detection of glycoproteins with an alternate detection system in one embodiment of the method.

FIG. 11 shows the detection of glycoproteins using biotinylated-wheat germ agglutinin (WGA-1:250 of 1 mg/ml) / DyLight™ 649-Streptavidin (1:4000 of 1 mg/ml). The gel was loaded as described for FIG. 10. The results show detection of all of the glycosylated proteins containing N-acetyl glucosamine sugar residues using this detection system Enhancement of signal sensitivity and intensity was observed by immersing the gel containing the separated proteins in a solution of a base in combination with an alcohol, compared to an alcohol alone. Glycoproteins were detected with lectins labeled with a variety of reporters (e.g. enzyme, fluorophore, radiolabel). The lectin method of detection of glycoproteins permits identifying specific glycan chains. As an example, Concanavalin A detects glucose/ mannose containing glycoproteins. As another example, peanut agglutinin detects galactose-containing glycoproteins. As another example, wheat germ agglutinin (WGA) binds selectively to dimers and trimers of N-acetylglucosamine sugar. The lectins can be simultaneously used for general glycoprotein staining or separately for more specific carbohydrate detection. The in-gel method of glycoprotein detection reduced the possibility of detecting non-glycosylated proteins and also provided a more accurate representation of the glycoproteins in the sample (e.g. lysate). The use of this in-gel method allows low nanogram level detection sensitivity and minimal non-specific binding of non-glycosylated proteins. The method also permits detecting glycoproteins that are difficult to transfer to membranes.

EXAMPLE X

Figure 12:
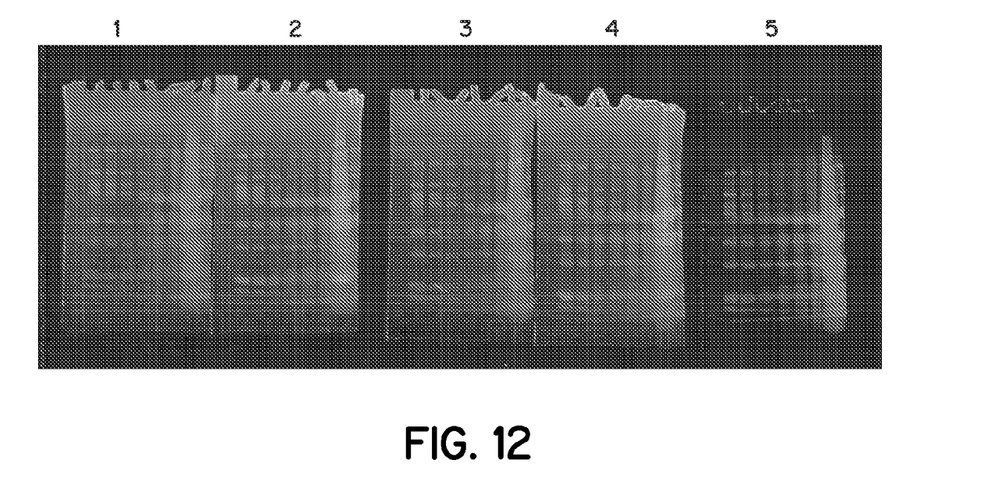
FIG. 12 shows dual detection of glycoproteins and total protein using two detection systems in one embodiment of the method.

The method was used in a multiplexing assay with a total fluorescent protein stain (FIG. 12). The gel was pre-treated with 25% v/v isopropanol and 25 mM NaOH; no additional treatment was performed for the protein staining. FIG. 12 shows the in-gel detection of glycoproteins along with total protein detection using biotinylated ConA/DyLight™ 649-SA (FIGS. 12.1 and 12.2) or biotinylated ConA/Alexa647-SA (FIGS. 12.3 and 12.4) and Krypton™ Protein Stain (Pierce Biotechnologies Inc.)(FIG. 12.1-12.5). This experiment showed that the in-gel detection method can be used in multiplexing experiment with a fluorescent protein stain.

EXAMPLE XI

Addition of base, along with alcohol, to the aqueous extracting media described in Examples I-VIII, is performed. The bases to be used include, but are not limited to alkoxide bases having an alkaline metal where the cation is lithium, sodium, potassium, rubidium and/or cesium, or amine cations where the cation can be Tris base. Examples of such bases include LiOH, KOH, and NaOH. The concentration of the base in the aqueous extracting media ranges from about 1 mM to about 200 mM. Inclusion of base in the aqueous extracting media result in protein detection sensitivities at least comparable to those achieved with alcohol alone and may exceed protein detection levels observed with alcohol alone.

EXAMPLE XII

Figure 13:
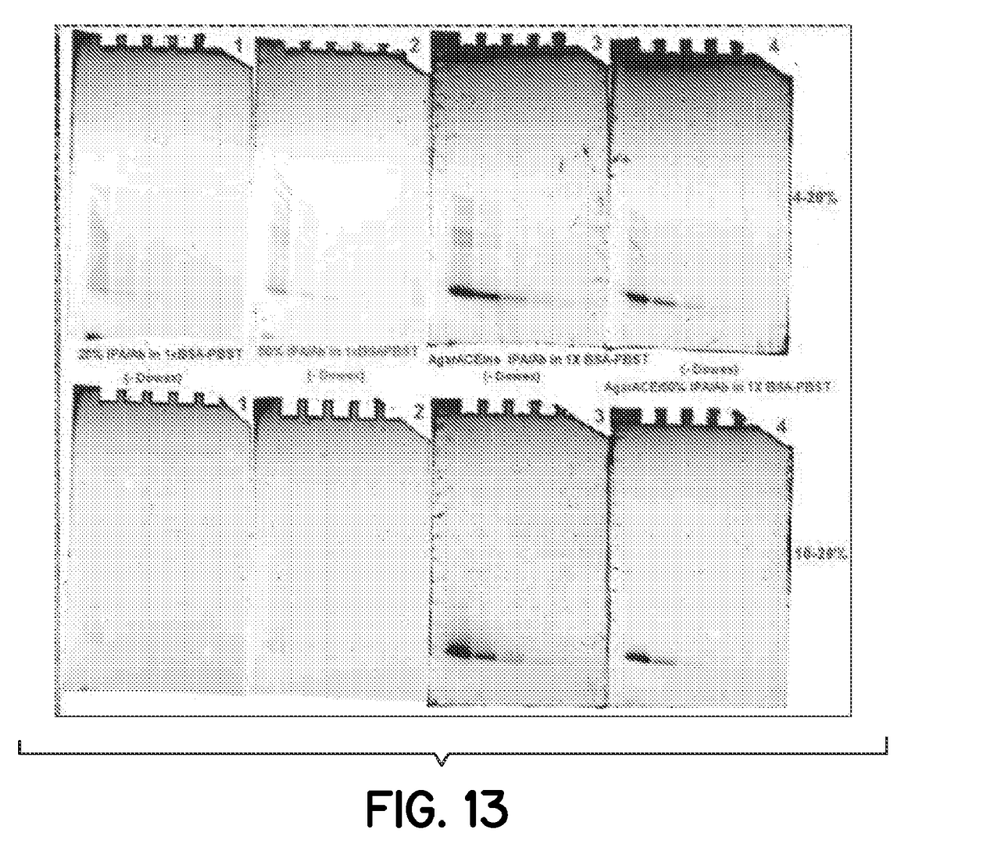
FIG. 13 shows detection of tumor necrosis factor α in one embodiment of the method.

The method was used in combination with agarase treatment of the gel. Tumor necrosis factor α(TNFα) was loaded onto both 4-20% and 10-20% PAGEgel™ composite polymer gels (PAGEgel, Inc., San Diego Calif.). Lanes 1-6 (from left to right) were loaded with 50 ng, 12.5 ng, 3.25 ng, 1 ng, 0.48 ng, and 0.2 ng TNFα, respectively. Following electrophoresis and a five minute wash in water (Milli-Q®), the gels 1-4 were treated as follows: gel 1 was incubated for fifteen minutes in 25% v/v isopropanol followed by a ten and then a fifteen minute wash with water (Milli-Q®); gel 2 was incubated for fifteen minutes in 50% v/v isopropanol followed by a ten and then a fifteen minute wash with water (Milli-Q®); gel 3 was washed for fifteen minutes with water (Milli-Q®) followed by a fifteen minute incubation with 0.0063 units/μl AgarACE™ (Promega) at 45° C. followed by 2×15 minute washes with water (Milli-Q®); gel 4 was washed for fifteen minutes with water (Milli-Q®) followed by a fifteen minute incubation with 0.0063 units/μl AgarACE™ (Promega) at 45° C. followed by fifteen minutes in 50% v/v isopropanol and fifteen minute wash with water (Milli-Q®).

Following treatment, the gels were probed with primary anti-TNFα polyclonal antibody (2 µg/ml) diluted in 1×BSA /PBS-0.05% v/v Tween®-20 and incubated for one hour with shaking at room temperature (about 20° C. to about 22° C.). The gels were then washed for 3×10 minutes in PBS-0.05% v/v Tween®-20 and then incubated in labeled secondary antibody DyLight™-647 (0.2 µg/ml) diluted in 1×BSA /PBS-0.05% v/v Tween®-20 for one hour with shaking at room temperature. The gels were then washed for 3×10 minutes in PBS-0.05% v/v Tween®-20. After the final wash, the gels were visualized on Typhoon (GE Healthcare).

FIG. 13 shows that agarase treatment (gel #3) of the polyacrylamide/agarose gel resulted in about an 8-fold increase in signal sensitivity and intensity as compared to the untreated gel (gel #1). Alcohol treatment of the gel after agarase treatment (gel #4) resulted in a 2-fold loss in sensitivity as compared to agarase treatment alone (gel #3); however, the sensitivity was greater compared to the untreated gel.

The method may also be performed on gel compositions other than polyacrylamide alone. For example, gels composed of either a combination of polyacrylamide and agarose, agarose or glyoxal agarose, may be used. In one embodiment, agarase may be included in the gel pretreatment step.

While the foregoing examples have illustrated use of the method in connection with interactions between proteins, it can also be used to study the interaction of other biomolecules, such as nucleic acids. The method may be used with assays in which interactions are detected by retardation phenomena. For example, the method can be used in the detection of DNA and RNA interactions with each other and/or with proteins. Such assays are practiced by a procedure in which the biomolecules of interest are incubated together in solution and then separated by gel electrophoresis. Retardation assays are based on the principle that the free biomolecule, e.g., DNA, will migrate faster than a biomolecule complex, e.g., of DNA and protein. By detecting a difference in band migration in the gel the existence of an interaction can be established.

All references, including publications, patent applications, and patents, cited herein are hereby incorporated by reference to the same extent as if each reference were individually and specifically indicated to be incorporated by reference and were set forth in its entirety herein.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for detecting a target biomolecule directly in a gel comprising (1) separating the target biomolecule from other substances by electrophoresis in a gel and, while the target molecule remains in the gel, (2) associating the target biomolecule with a probe having a label which is capable of providing a detectable signal, (3) removing any non-associated probe from the gel, and (4) detecting the presence of the target biomolecule by observing a signal attributable to the presence of the labeled probe associated with the target biomolecule; wherein, prior to associating the target biomolecule with the probe and while the target biomolecule remains separated in the gel, (A) the gel is shrunk by at least about 10% by immersing the gel in a water miscible, aqueous extracting medium containing at least about 1 mM base, and then (B) the gel is washed with water for a sufficient time to restore the gel to substantially its original size, the method detecting at least one target biomolecule directly in the gel.

2. The method of claim 1 wherein the concentration of the base is in the range of about 1 mM to about 200 mM.

3. The method of claim 1 wherein the concentration of the base is in the range of about 25 mM to about 150 mM.

4. The method of claim 1 wherein the base is an alkoxide having an alkaline metal cation.

5. The method of claim 1 wherein the base is selected from the group consisting of lithium hydroxide, sodium hydroxide, potassium hydroxide, rubidium hydroxide, cesium hydroxide, and combinations thereof.

6. The method of claim 1 wherein the base has an amine cation.

7. The method of claim 6 wherein the base is Tris (Hydroxymethyl)aminomethane) base.

8. The method of claim 1 wherein the biomolecule is selected from the group consisting of a protein, a polypeptide, a nucleic acid, and combinations thereof.

9. The method of claim 8 wherein the protein is a glycoprotein.

10. The method of claim 1 wherein the gel is shrunk is by at least about 10% and less than about 50%.

11. The method of claim 1 wherein the gel is shrunk by at least about 15% and less than about 35%.

12. The method of claim 1 wherein the aqueous extracting medium comprises water and a short chain alcohol at a concentration ranging from about 10% v/v to about 75% v/v.

13. The method of claim 12 wherein the alcohol is selected from the group consisting of methanol, ethanol, isopropanol, and combinations thereof present at a concentration ranging from about 35% v/v to about 65% v/v.

14. The method of claim 12 wherein the alcohol is isopropanol present at a concentration of about 50% v/v.

15. The method of claim 1 wherein the signal is at least one of fluorescent, luminescent, or radioactive.

16. The method of claim 1 wherein the label is an enzyme and a fluorescent or luminescent signal is generated by action of the enzyme on a substrate.

17. The method of claim 16 where the enzyme is alkaline phosphatase and the signal is fluorescent.

18. The method of claim 16 where the enzyme is horseradish peroxidase and the signal is luminescent.

19. The method of claim 16 wherein the substrate is luminol.

20. A method for detecting a target biomolecule directly in a medium in which it has been separated from other substances, the method comprising, prior to binding the target biomolecule to a probe and while the target biomolecule remains in the medium, immersing the medium in a water miscible aqueous extracting medium and a base at a concentration sufficient to shrink the medium by at least about ten percent, and then washing to restore the medium to substantially its original size, and thereafter, incubating the medium with probe for the target biomolecule.

21. The methods of any of claims 1 or 20 wherein prior to binding the target molecule to a probe and while the target biomolecule remains in the medium, the medium is treated with agarase.

22. The method of claim 21 wherein the medium is immersed in a water miscible aqueous extracting medium without a base.

23. The methods of any of claims 1 or 20 wherein a plurality of target biomolecules is detected with a plurality of probes.

24. The methods of any of claims 1 or 20 wherein the gel and/or medium composition is selected from the group consisting of polyacrylamide, polyacrylamide/agarose, agarose, and glyoxal agarose.

* * * * *